(12) United States Patent
Glund et al.

(10) Patent No.: US 6,458,568 B1
(45) Date of Patent: Oct. 1, 2002

(54) METHOD FOR THE PRODUCTION OF BACCATIN-III BY ENZYMATIC SYNTHESIS

(75) Inventors: Konrad Glund, Halle; Matthias Hoffmann, Weissenfels; Wolfram Weckwerth; Rainer Zocher, both of Berlin, all of (DE)

(73) Assignee: Institut fuer Bioanalytik, Umwelt-Toxikologie und Biotechnologie Halle GmbH, Halle (DE)

( * ) Notice: Subject to any disclaimer, the term of this patent is extended or adjusted under 35 U.S.C. 154(b) by 0 days.

(21) Appl. No.: 09/311,084

(22) Filed: May 13, 1999

(30) Foreign Application Priority Data

May 22, 1998 (DE) .......................................... 198 22 881

(51) Int. Cl.$^7$ ............................................... C12P 17/02
(52) U.S. Cl. ....................... 435/123; 435/189; 435/117; 435/118; 549/510
(58) Field of Search ................................ 435/123, 189, 435/117, 118; 549/510

(56) References Cited

U.S. PATENT DOCUMENTS 5,302,520 A * 4/1994 Goux ........................... 435/195
5,480,639 A * 1/1996 ElSohly ..................... 424/195.1
5,549,830 A * 8/1996 Carver ......................... 210/641

OTHER PUBLICATIONS

Nanduri et al., Biotechnol. Bioeng. (1995), 48(5), 547–50.*
Zocher et al., Biochem. Biophys. Res. Commun. 1996, vol. 229, pp. 16–20.*
Hanson et al., J. Biol. Chem. (1994), 269(35), 22145–9.*

* cited by examiner

Primary Examiner—Irene Marx
(74) Attorney, Agent, or Firm—Jordan and Hamburg LLP

(57) ABSTRACT

A method for the continuous synthesis of baccatin-III is performed by means of the enzymatic acetylations of 10-deacetyl baccatin-III (10-DAB) in an enzyme reactor. This objective is accomplished by a method, for which an aqueous reaction batch is used, which contains a partially purified or a very pure acetyl transferase from a Taxus species and synthesis components, especially 10-DAB, acetyl compounds or optionally an acetyl coenzyme A, which can be regenerated, a protective colloid and optionally a buffer substance in solution. The solution is separated by a semipermeable membrane from an organic solvent, which serves as extraction agent for baccatin-III, the reaction batch being regenerated at regular intervals in an aqueous buffer system and the solvent continuously being exchanged. By conducting the reaction, the product can be removed continuously from the reaction batch for the partial synthesis of taxol and taxoter. By the above method, achievable yields are increased significantly.

8 Claims, No Drawings

METHOD FOR THE PRODUCTION OF BACCATIN-III BY ENZYMATIC SYNTHESIS

FIELD OF THE INVENTION

The invention relates to a new method for the continuous synthesis of baccatin-III by means of the enzymatic acetylation of 10-deacetyl baccatin-III (10-DAB) in an enzyme reactor.

BACKGROUND OF THE INVENTION

10-DAB and baccatin-III are intermediates for the biosynthesis of taxol and can be isolated in different concentrations from yews (Taxus spec.) (0.0002% of baccatin-III from the bark of *Taxus baccata*, 0.02% of DAB from the needles and branches, Kingston, D.G.I. Pharm. Ther. 1991, 52, 1–34).

Taxans, especially taxol (paclitaxel) are cyclotoxic diterpenes from the yew, of which a few inhibit cell replication on a molecular basis, in that they inhibit growing cells in the G2/M phase of the cell cycle. They therefore have an anti-tumor effect and are used increasingly for the treatment of a series of carcinomas (ovarian, breast, bronchial and lung carcinomas).

Taxans and related active ingredients are produced by plants of the Taxus species and are constituents of different parts of such plants. It is therefore a technically and economically meaningful objective to develop the prerequisites for a rational extraction of taxans (particularly taxol) from Taxus plants and, from this, to derive methods for the recovery of this material and its analogs.

At the present time taxol is obtained on a larger scale by working up the bark of *Taxus brevifolia* Nutt. Extrapolations indicate that about 9 tons of bark have to be worked up in order to produce 1 kg of taxol.

Since this method foreseeably would lead to the destruction of the existing stands of yews, alternatives were sought for obtaining taxol completely or partially by chemical synthesis (Holton, R. A and Ojima, I; EP-A 400971, 1990).

However, because of its complexity, the first-named possibility of obtaining taxol fully by synthesis has foreseeably not proven to be suitable for covering the already existing demand at justifiable costs.

Partial synthesis, starting out from 10-DAB, is more successful. The concentration of 10-DAB in the needles of the European yew (*Taxus baccata*) is about 6 to 10 times that of taxol in the bark of *Taxus breviflora* Nutt. 10-DAB can thus be extracted in larger amounts from a source of raw materials, which can be regenerated.

The purification of 10-DAB is significantly simpler and more economic than the extraction of taxol, since there is no need for the expensive separation of the structurally very similar cephalomannin. Taxol has to be made available in a highly purified form for formulating the drug directly. On the other hand, the purity of 10-DAB only has to be adequate so that it can be used as a starting material for the partial synthesis. Moreover, with 10-DAB, one starts out from a molecule, the complete synthesis is possible only at a cost, which is hardly justifiable economically.

The chemical synthesis of baccatin-III is accomplished successfully by the specific acetylation of the hydroxyl group at position 10 of 10-DAB.

However, it is a disadvantage that the chemical acetylation of the substrate is nonspecific. The four hydroxyl groups in the 10-DAB were shown to have different reactivities in an acetylation reaction. The most reactive one is the C-7 hydroxyl group, followed by the hydroxyl groups at positions C-10 and C-13. On the other hand, the hydroxyl group at C-1 was not acetylated under any of the conditions investigated. Undesirable acetylations at C-7 and C-13 must be prevented by correspondingly expensive chemical blocking of the hydroxyl groups. After a successful acetylation at C-10, the blocking groups must be removed once again.

Basically, the reaction mechanism of the acetyl transferase, isolated from *Taxus baccata* (Zocher, R. Weckerth, W, Hacker, C., Kammer, B., Horbogen, T., Eweld, D., B.B.R.C., 1996, 229, 16–20), that is, 1. The conversion of 10-DAB into baccatin-III outside of the organism is possible (in vitro).
2. The acetyl transferase from *Taxus baccata* is highly specific, that is, the OH group at position C-10 of the 10-DAB substrates is acetylated exclusively (the structures are given in Formulas 1 and 2).

Formula 1: Structure of 10-DAB

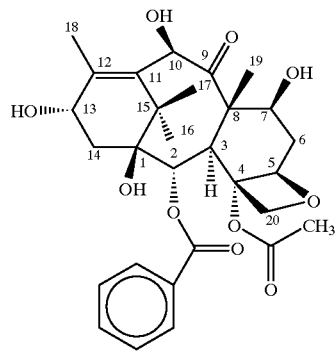

Formula 2: Structure of Baccatin-III

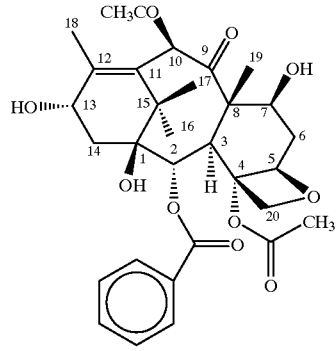

There are, however, still some problems with a rational, technical use of the enzyme:

- In the case of an enzymatic batch method, the enzyme used is lost during the working up.
- The process time of a batch method is of the order of hours.
- During longer incubation times, contaminations by microorganisms occurs in the batch method.
- Immobilization to improve the technical properties always leads to severe losses in activity.

It was therefore an object of the invention to carry out successfully the enzymatic acetylation of 10-DAB with crude cell extracts from the roots of yews (Taxus spp).

It was therefore a further object of the invention to develop an industrially usable method for the enzymatic synthesis of baccatin-III by the acetylation of 10-DAB, which avoids these disadvantages.

SUMMARY OF THE INVENTION

These objects of the invention are accomplished by a method, in which an aqueous reaction batch is used, which contains a partially purified or a very pure acetyl transferase from the Taxus species and synthesis components, especially 10-DAB, acetyl compounds or optionally an acetyl co-enzyme A, which can be regenerated, and optionally a buffer in solution, and is separated using a semipermeable membrane from an organic solvent, which is used to extract the baccatin-III, the reaction batch being regenerated at regular intervals in an aqueous buffer system and the solvent being changed continuously.

Surprisingly, it was noted that the acetyl transferase, obtained from *Taxus baccata*, is stable even in the presence of organic solvents and that the operational stability of the enzyme is increased drastically, if the aqueous reaction batch, which is in a semipermeable membrane, is surrounded by a suitable organic solvent and regenerated at defined times by dialysis in the aqueous buffer system. The presence of the organic solvent prevents microbial contamination.

DETAILED DESCRIPTION OF THE INVENTION

Accordingly, the methods of the invention provide for the following processes.

the enzymatic acetylation of 10-DAB to form baccatin-III by the acetyl transferase from *Taxus baccata*, the extraction of the baccatin-III, formed in the aqueous batch by enzymatic catalysis, by a suitable organic solvent, The continuous replacement of the solvent containing the baccatin-III and the continuous removal of the product.

a regeneration of the reaction batch by dialysis in an aqueous buffer system.

Aside from the acetyl transferase, the reaction batch should preferably contain an enzyme for regenerating acetyl coenzyme A (CoA), which activates short-chained fatty acids (acetic acid, propionic acid and acrylic acid), that is, converts them into the acyl CoA thioester.

A system for generating acetyl co-enzyme A (CoA), consists of:

the coenzyme A the acetyl coenzyme A synthetase or ligase acetate a source of energy, namely adenosine-5-triphosphate (ATP), since energy is consumed for activating the fatty acids.

The present method permits the acetyl transferases to be used continuously or semi-continuously for the production of baccatin-III.

The method, for using isotope-labeled acetyl CoA, is very suitable for synthesizing radioactively-labeled baccatin-III.

The preferred variation consists of using acetyl transferases from yews (Taxus species).

It is advantageous if an over-expressed, recombinant acetyl transferase is used as acetyl transferase.

An over-expressed, recombinant acetyl transferase is the enzyme, which is used in a reaction batch and has been produced by genetic engineering methods in an organism, which differs from the Taxus species, for example, in a fungus or a yeast.

The dialysis or semipermeable membrane is permeable for the reaction products but not for the enzyme. Preferably, it consists of a cellulose ester.

The dialysis or semipermeable membrane is surrounded by a suitable organic solvent. All solvents, in which the product is soluble and which form two-phase systems with water, are suitable.

Preferably, chloroform and heptane are used as organic solvents. A 1:4 mixture of chloroform and heptane is particularly suitable.

The advantages of the inventive method over the chemical acetylations, which are used at the present time industrially, lies in the specificity of the acetylations. By conducting the reaction suitably in an enzyme reactor, the product can be removed continuously from the reaction batch and used directly for the partial synthesis of the taxol and the taxoter. By these means, the process time (at least of the order of weeks) and the achievable yields (mg of product per mg of enzyme used) can be increased significantly.

The method is described by means of the following examples but is not limited to these.

EXAMPLE

All processes are carried out at 4° C. *Taxus baccata* roots (10 g), which had previously been stored at −80° C., are crushed in a mortar with the repeated addition of liquid nitrogen. With the addition of beach sand, the material is ground to a fie powder and subsequently taken up in 50 mM of tris/HCl buffer (4 mL of buffer per gram of fresh roots) (the composition of the buffer is given in Biochem. Biophys. Res. Commun. 229 16–20 (1996)). The suspension is stirred carefully for one hour, After the cell debris has been removed by centrifuging at 10,000 rpm for 20 minutes, a precipitation with 30 percent ammonium sulfate is carried out with the supernatant solution (15 minutes on ice), The pellet is separated by centrifuging (10,000 rpm for 20 minutes) and a 30% to 90% ammonium sulfate precipitation is carried out with the remaining supernatant solution (1 hour on ice). After centrifuging once again (10,000 rpm for 20 minutes) the pellet is separated from the supernatant solution and taken up in a little buffer (see above). This resuspended 30% to 90% ammonium sulfate precipitate is desalinated with a small Sephadex G 25 column (Pharmacie, PD 10 column). All enzymatic reactions are carried out with the resulting fraction.

The synthesis in the enzyme reactor is carried out under the following conditions:

The solvent used in the process is a 1:4 mixture of chloroform and heptane. The dialysis bag contains an aqueous solution of the following components:

1 mL of acetyl CoA DAB-O transferase (protein concentration of 100 $\mu$g/mL, DEAE fraction) in 0.05 M HEPES buffer of pH 8;

1% bovine serum albumin,

50 $\mu$M DAB;

5% ethanol;

50 $\mu$M acetyl CoA

2 $\mu$M [$^3$H-acetyl)-CoA

The radioactive baccatin III formed (with the $^3$H) goes into the organic phase, which is changed repeatedly while the reactor is operated. The reaction product is recovered by reverse phase HPLC, since a portion of the 10-deacetyl baccatin III educt also goes over into the organic phase and can be returned to the process after it has been separated.

After being incubated for 12 hours at room temperature, the dialysis membrane with the enzyme is transferred into a glass vessel with 0.05 M HEPES buffer having a pH of 8 and remains there for 12 hours.

The dialysis step serves to regenerate the reaction batch, primarily the coenzyme A, which is formed, being removed.

After that, the batch is mixed with new substrate and once again brought into the enzyme reactor. Two enzyme portions are used alternately, so that the reaction can be kept going continuously.

Under the conditions named, approximately 1 mg of baccatin III per hour can be produced per mg of acetyl transferase.

The enzymatic acetylation takes place specifically at position 10. Other substrates, such as taxol, baccatin III with free OH groups, were used as in the example and not acetylated. 10-Deacetyl taxol, used as in the example, is significantly weaker as a substrate than is 10-deacetyl baccatin III.

What is claimed is:

1. A method for the production of baccatin-III by enzymatic acetylation of 10-deacetyl baccatin-III, comprising,
   (a) selectively aceylating 10-deacetyl baccatin-III at position C-10 to produce baccatin-III, by contacting 10-deacetyl baccatin-III with an acetyl transferase enzyme extracted from a Taxus species, in an aqueous reaction batch, wherein the aqueous reaction batch is separated from a composition comprising an organic solvent capable of extracting baccatin-III by a semipermeable membrane positioned therebetween,
   (b) extracting the baccatin-III produced by step (a) from the aqueous reaction batch into the organic solvent capable of extracting baccatin-III, wherein the semipermeable membrane selectively passes baccatin-III, and retains the acetyl transferase enzyme;
   (c) recovering the baccatin-III from the organic solvent;
   wherein said aqueous reaction batch comprises the acetyl transferase enzyme, 10-deacetyl baccatin-III, and acetyl coenzyme A.

2. The method of claim 1 wherein the aqueous reaction batch further comprises components effective to regenerate acetyl coenzye A, comprising acetyl coenzyme A synthetase, acetate, acetyl coenzyme A ligase, and adenosine-5-triphosphate in amounts effective to regenerate the acetyl coenzyme A in the aqueous reaction batch from coenzyme A produced by the production of baccatin-III.

3. The method of claim 1 further comprising the step of:
   (d) replacing components in the aqueous reaction batch depleted by the production of baccatin-III by adding the components as required to the aqueous reaction batch.

4. The method of claim 3 further comprising regenerating acetyl coenzyme A in the aqueous reaction batch by removing accumulated coenzyme A from the aqueous reaction batch by dialyzing against an aqueous buffer separated from the aqueous reaction batch by the semipermeable membrane.

5. The method of claim 1 wherein the organic solvent comprises a mixture of chloroform and heptane in a ratio of 1:4.

6. The method of claim 1, wherein the acetyl transferase enzyme is extracted from *Taxus baccata* roots.

7. The method of claim 1 wherein the sempermeable membrane is cellulose ester.

8. The method of claim 1 further comprising removing accumulated coenzyme A from the aqueous reaction batch by dialyzing against an aqueous buffer on a continuous basis.

* * * * *